(12) United States Patent  
Yano et al.

(10) Patent No.: US 11,045,375 B2  
(45) Date of Patent: Jun. 29, 2021

(54) ROBOTIC OPERATING TABLE, AND ROBOTIC OPERATING TABLE OPERATION DEVICE

(71) Applicants: MEDICAROID CORPORATION, Kobe (JP); SYSMEX CORPORATION, Kobe (JP)

(72) Inventors: Yutaro Yano, Kobe (JP); Yoshiyuki Tamura, Kobe (JP); Toru Mizumoto, Kobe (JP); Kenichi Nakagawa, Kobe (JP); Yuuki Suzuki, Kyoto (JP); Hidetoshi Yoshioka, Takatsuki (JP); Yuko Hidaka, Osaka (JP); Yuichi Kageyama, Kyoto (JP)

(73) Assignees: MEDICAROID CORPORATION, Kobe (JP); SYSMEX CORPORATION, Kobe (JP)

( * ) Notice: Subject to any disclaimer, the term of this patent is extended or adjusted under 35 U.S.C. 154(b) by 553 days.

(21) Appl. No.: 15/905,890

(22) Filed: Feb. 27, 2018

(65) Prior Publication Data

US 2018/0243149 A1 Aug. 30, 2018

(30) Foreign Application Priority Data

Feb. 28, 2017 (JP) .............................. JP2017-035607

(51) Int. Cl.
*A61G 13/04* (2006.01)
*A61G 13/10* (2006.01)
(Continued)

(52) U.S. Cl.
CPC ............ *A61G 13/04* (2013.01); *A61B 5/0036* (2018.08); *A61B 6/0487* (2020.08);
(Continued)

(58) Field of Classification Search
CPC ... A61B 5/0036; A61B 5/0555; A61B 6/0457; A61B 6/0407; A61G 13/04;
(Continued)

(56) References Cited

U.S. PATENT DOCUMENTS 6,302,579 B1 * 10/2001 Meyer .................. A61B 6/4429  
378/195  
7,669,261 B2 3/2010 Früh et al.  
(Continued)

FOREIGN PATENT DOCUMENTS

EP 1028684 B1 3/2004  
JP H05-301182 A 11/1993  
(Continued)

OTHER PUBLICATIONS

The Japanese Office Action dated May 14, 2019 in a counterpart Japanese patent application.
(Continued)

*Primary Examiner* — Chih-Cheng Kao  
(74) *Attorney, Agent, or Firm* — Metrolex IP Law Group, PLLC

(57) ABSTRACT

A robotic operating table according to one or more embodiments may include: a patient placement table; a robotic arm comprising a plurality of joints, and having a first end supported on a base and a second end supporting the table; and an operation device comprising a preset position registration setting unit that registers an anesthetization position, a surgical operation position, and an imaging position and sets one of the registered anesthetization, surgical operation, and imaging positions as a movement destination of the table, and a move-operation receiving unit that receives, from a user, a move operation to move the table. When the move-operation receiving unit is operated while one of the registered anesthetization, surgical operation, and imaging
(Continued)

positions is set as the movement destination of the table, the robotic arm may move the table to the set one of the registered anesthetization, surgical operation, and imaging positions.

27 Claims, 8 Drawing Sheets

(51) Int. Cl.
  *A61B 5/00* (2006.01)
  *A61B 6/04* (2006.01)
  *A61B 6/00* (2006.01)
  *A61B 5/055* (2006.01)

(52) U.S. Cl.
  CPC ............ *A61G 13/104* (2013.01); *A61B 5/055* (2013.01); *A61B 6/4441* (2013.01); *A61G 2203/12* (2013.01); *A61G 2203/14* (2013.01); *A61G 2203/20* (2013.01); *A61G 2210/50* (2013.01)

(58) Field of Classification Search
  CPC .............. A61G 13/104; A61G 2203/12; A61G 2203/14; A61G 2203/20; A61G 2210/50
  See application file for complete search history.

(56) References Cited

U.S. PATENT DOCUMENTS

| | | | |
|---|---|---|---|
| 7,860,550 B2 | 12/2010 | Saracen et al. | |
| 8,126,114 B2 | 2/2012 | Naylor et al. | |
| 8,160,205 B2 | 4/2012 | Saracen et al. | |
| 9,326,907 B2 | 5/2016 | Marle | |
| 2003/0195644 A1* | 10/2003 | Borders | A61G 13/107 700/90 |
| 2005/0228255 A1* | 10/2005 | Saracen | A61B 6/0457 600/407 |
| 2010/0299014 A1* | 11/2010 | Bouvier | A61B 6/4405 701/25 |
| 2011/0004070 A1* | 1/2011 | Rist | G16H 40/20 600/300 |
| 2015/0000038 A1 | 1/2015 | Obi | |
| 2015/0201899 A1* | 7/2015 | Uchinomiya | G06F 19/321 378/62 |
| 2015/0327818 A1 | 11/2015 | Buck et al. | |

FOREIGN PATENT DOCUMENTS

| | | |
|---|---|---|
| JP | H06-071584 A | 3/1994 |
| JP | 2001-522648 A | 11/2001 |
| JP | 2009-131599 A | 6/2009 |
| JP | 2009-131718 A | 6/2009 |
| JP | 2009-291281 A | 12/2009 |
| JP | 2014-100301 A | 6/2014 |
| JP | 2014-215799 A | 11/2014 |
| JP | 2016-054860 A | 4/2016 |
| WO | 2013/018908 A1 | 2/2013 |

OTHER PUBLICATIONS

The Japanese Office Action dated Mar. 5, 2019 in a counterpart Japanese patent application.

* cited by examiner

ROBOTIC OPERATING TABLE, AND ROBOTIC OPERATING TABLE OPERATION DEVICE

CROSS REFERENCE TO RELATED APPLICATIONS

This application claims priority to Japanese Patent Application No. 2017-035607 filed on Feb. 28, 2017, entitled "ROBOTIC OPERATING TABLE, AND ROBOTIC OPERATING TABLE OPERATION DEVICE", the entire contents of which is incorporated herein by reference.

BACKGROUND

One or more embodiments relate to a robotic operating table, a hybrid operation room system, and a robotic operating table operation device.

Japanese Patent Application Publication No. 2014-100301 discloses a hybrid operation room including a combination of a radiographic fluoroscopic imaging apparatus and an operating table. The operating table of the hybrid operation room according to Japanese Patent Application Publication No. 2014-100301 slides a movable table in parallel to horizontal directions along a base fixed to the floor. The base is freely extendable and contractible in the vertical direction and is configured to raise and lower the table in the vertical direction.

SUMMARY

A robotic operating table according to one or more embodiments may include: a patient placement table; a robotic arm comprising a plurality of joints, and having a first end supported on a base and a second end supporting the table; and an operation device comprising a preset position registration setting unit that registers an anesthetization position, a surgical operation position, and an imaging position and sets one of the registered anesthetization, surgical operation, and imaging positions as a movement destination of the table, and a move-operation receiving unit that receives, from a user, a move operation to move the table. In one or more embodiments, when the move-operation receiving unit is operated while one of the registered anesthetization, surgical operation, and imaging positions is set as the movement destination of the table, the robotic arm may move the table to the set one of the registered anesthetization, surgical operation, and imaging positions.

A robotic operating table according to one or more embodiments may include: a patient placement table; a robotic arm comprising a plurality of joints, and having a first end supported on a base and a second end supporting the table; an operation device including a preset position registration setting unit that registers a preset position and sets the preset position as a movement destination of the table, and a move-operation receiving unit that receives, from a user, a move operation to move the table; and a sound output unit. In one or more embodiments, when one or more embodiments, the move-operation receiving unit is operated with the preset position set as the movement destination, the sound output unit may output a sound message indicating that the table is going to move to the preset position.

A hybrid operation system according to one or more embodiments may include: a robotic operating table; and at least one of a radiographic imaging apparatus that captures a radiographic projection image of a patient and a magnetic resonance imaging apparatus that captures a magnetic resonance image of the patient. In one or more embodiments, the robotic operating table may include: a patient placement table; a robotic arm comprising a plurality of joints, and having a first end supported on a base and a second end supporting the table; and an operation device including a preset position registration setting unit that registers an anesthetization position, a surgical operation position, and an imaging position and sets one of the registered anesthetization, surgical operation, and imaging positions as a movement destination of the table, and a move-operation receiving unit that receives, from a user, a move operation to move the table. In one or more embodiments, when the move-operation receiving unit is operated while one of the registered anesthetization, surgical operation, and imaging positions is set as the movement destination of the table, the robotic arm may move the table to the one of the registered anesthetization, surgical operation, and imaging positions.

A robotic operating table operation device according to one or more embodiments may include: a preset position registration setting unit that registers an anesthetization position, a surgical operation position, and an imaging position and sets one of the registered anesthetization, surgical operation, and imaging positions as a movement destination of a patient placement table of the robotic operating table; a move-operation receiving unit that receives, from a user, a move operation to move the table; and a display. In one or more embodiments, the robotic operating table may include the table, and a robotic arm comprising a plurality of joints, and having a first end supported on a base and a second end supporting the table. In one or more embodiments, when one of the registered anesthetization, surgical operation, and imaging positions is set as a movement destination of the table, the display may display the set position of the movement destination of the table.

DETAILED DESCRIPTION

Figure 1:
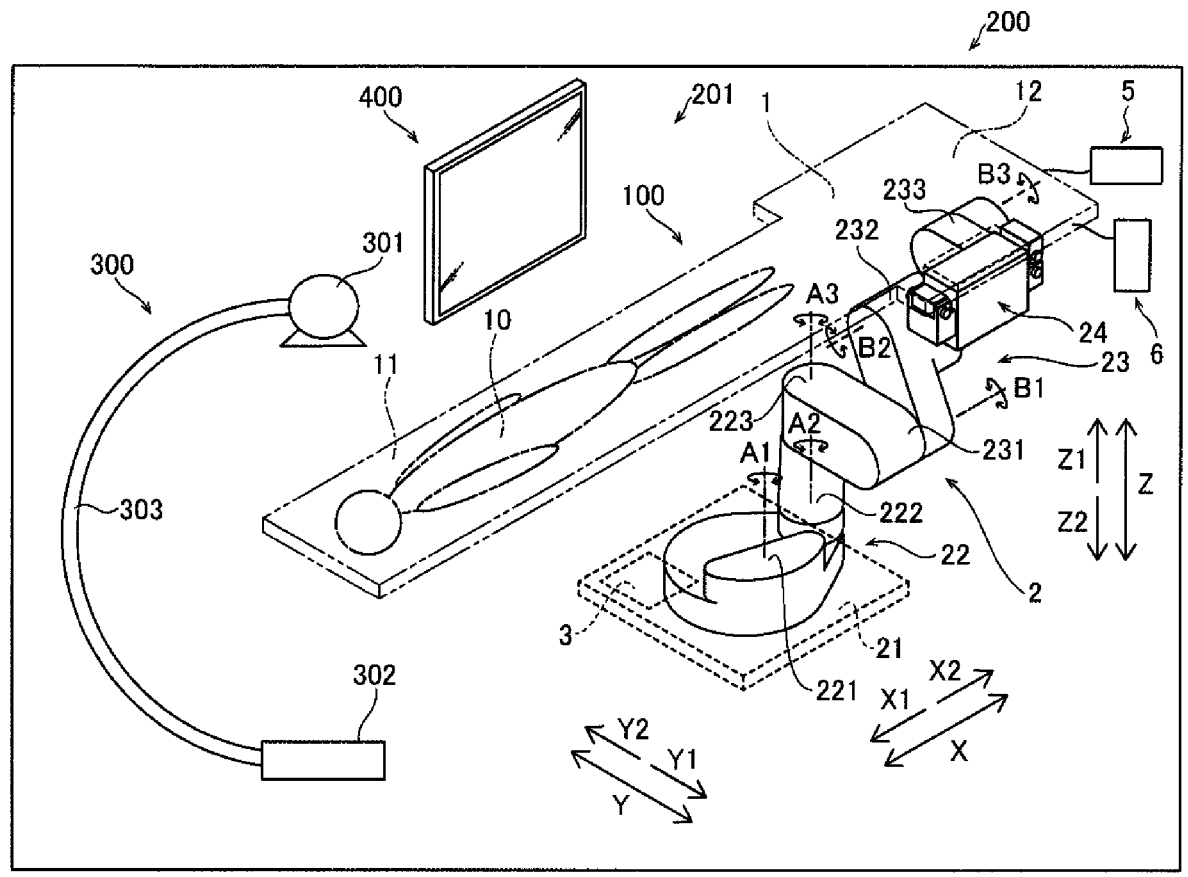
FIG. 1 is a diagram schematically illustrating hybrid operation room including a robotic operating table according to one or more embodiments.

One or more embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings may not be to scale, and are not intended to impose restrictions on the disclosed embodiments. For this reason, specific dimensions and the like should be interpreted with the accompanying descriptions taken into consideration. In addition, the drawings may include parts whose dimensional relationship and ratios are different from one drawing to another.

Prepositions, such as "on", "over" and "above" may be defined with respect to a surface, for example a layer surface, regardless of the orientation of the surface in space.

(Configuration of Operating Table)

The following describes the configuration of a robotic operating table 100 according to one or more embodiments with reference to FIGS. 1 to 10.

As illustrated in FIG. 1, the robotic operating table 100 is provided in a hybrid operation room 200. The hybrid operation room 200 is provided with a radiographic imaging apparatus 300 that captures a radiographic projection image of a patient 10. The hybrid operation room 200 may also be provided with a display 400 for displaying information on a surgical operation. In other words, the hybrid operation room 200 may be provided with a hybrid operation room system 201 including the robotic operating table 100 and the radiographic imaging apparatus 300. The display 400 may be suspended by, for example, an arm (not illustrated) and may be movable inside the hybrid operation room 200. The robotic operating table 100 is used as a table for a surgical operation performed in, for example, surgery or internal medicine. The robotic operating table 100 is capable of moving a table 1 to a placement position at which to place the patient 10 onto the table 1, and moving the patient 10 to, for example, a patient receiving position, an anesthetization position, a surgical operation position, a test position, a treatment position, a radiographic imaging position, and a patient passing position while the patient 10 is placed on the table 1. The robotic operating table 100 is also capable of tilting the patient 10 while the patient 10 is placed on the table 1.

Figure 3:
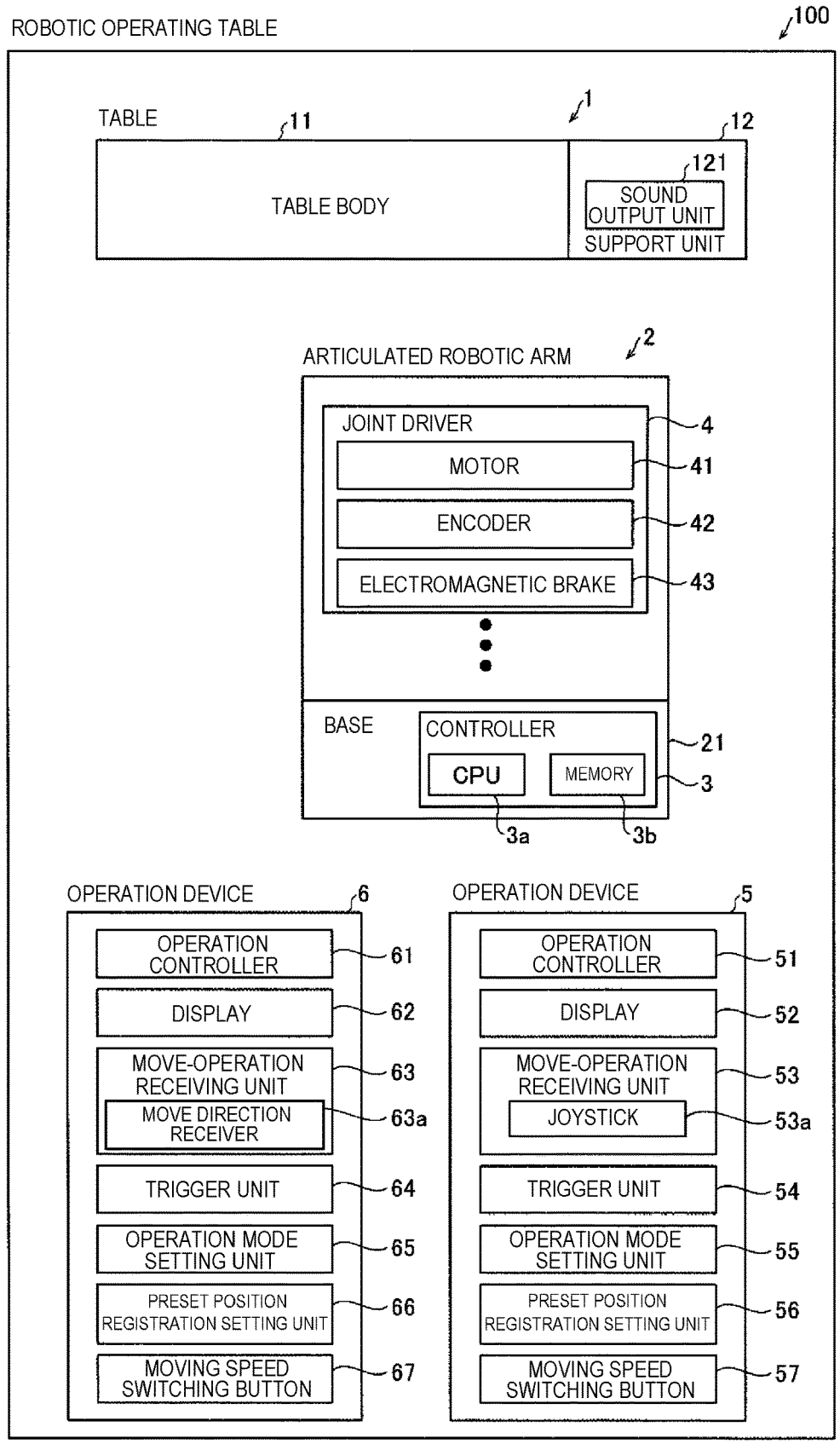
FIG. 3 is a block diagram illustrating the robotic operating table according to one or more embodiments.

The robotic operating table 100 includes the patient placement table 1, a robotic arm 2, a controller 3, an operation device 5, and an operation device 6. The robotic arm 2 is an articulated robotic arm, which includes a plurality of joints. The table 1 includes a table body 11 and a support unit 12 supporting the table body 11. As illustrated in FIG. 3, the table 1 also includes a sound output unit 121. As illustrated in FIG. 1, the robotic arm 2 includes a base 21, a horizontal articulated assembly 22, a vertical articulated assembly 23, and a pitch mechanism 24. The horizontal articulated assembly 22 includes horizontal joints 221, 222 and 223. The vertical articulated assembly 23 includes vertical joints 231, 232 and 233. The radiographic imaging apparatus 300 includes an X-ray irradiation unit 301, an X-ray detection unit 302, and a C-arm 303. The operation devices 5 and 6 are each an exemplary "robotic operating table operation device" in the claims. The horizontal joints 221 to 223 and the vertical joints 231 to 233 may be examples of "joint" in one or more recited embodiments.

Figure 2:
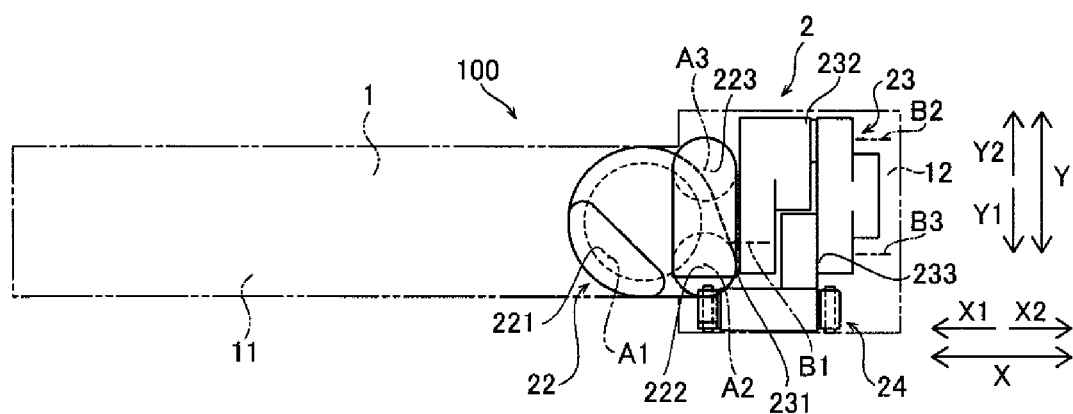
FIG. 2 is a plan view illustrating the robotic operating table according to an embodiment.

As illustrated in FIGS. 1 and 2, the table 1 has a substantially rectangular flat plate shape. The table 1 has a substantially flat upper surface. The longitudinal direction of the table 1 is aligned with an X direction, and the transverse direction of the table 1 is aligned with a Y direction. The table 1 may be rotatable about an axis extending in a vertical direction (Z direction). In this example, the X direction is defined to be a horizontal direction along the longitudinal direction of the table 1, and the Y direction is defined to be a horizontal direction along the transverse direction of the table 1. Thus, the X direction and the Y direction are directions with reference to the table 1.

As illustrated in FIG. 1, the patient 10 is placed onto the table body 11 of the table 1. The table body 11 is disposed on an X1 direction side of the table 1. The table body 11 has a substantially rectangular shape. The table body 11 may be made of an X-ray transmittable material. The table body 11 may be made of, for example, a carbon material (graphite). The table body 11 may be made of, for example, carbon fiber reinforcement plastic (CFRP). With this configuration, a radiographic image of the patient 10 may be captured while the patient 10 is placed on the table body 11.

The support unit 12 of the table 1 is connected with the robotic arm 2. The support unit 12 is disposed on an X2 direction side of the table 1. The support unit 12 has a substantially rectangular shape. The support unit 12 supports the table body 11. The support unit 12 may be made of a material having an X-ray transmissivity smaller than that of the table body 11. The support unit 12 may be made of, for example, metal. The support unit 12 may be made of, for example, a steel material or an aluminum material.

The table 1 is moved by the robotic arm 2. Specifically, the table 1 is movable in the X direction along a horizontal direction, the Y direction along a horizontal direction orthogonal to the X direction, and the Z direction along a vertical direction orthogonal to the X direction and the Y direction. The table 1 may freely rotate (roll) about an axis extending in the X direction. The table 1 may also freely rotate (pitch) about an axis extending in the Y direction. The table 1 may also freely rotate (yaw) about an axis extending in the Z direction.

The sound output unit 121 generates notification sound to notify movement of the table 1. Specifically, the sound output unit 121 generates notification electronic sound and a notification sound message. The sound output unit 121 may include a speaker. The sound output unit 121 generates the notification sound under control of the controller 3.

The robotic arm 2 moves the table 1. As illustrated in FIG. 1, the robotic arm 2 has one end supported on the base 21 fixed to the floor, and the opposite end supporting the table 1. Specifically, the robotic arm 2 is supported on the base 21 to be rotatable about a base rotation axis (rotation axis A1) substantially perpendicular to an installation surface on which the base 21 is installed. The robotic arm 2 supports the vicinity of one end of the table 1 on the X2 direction side in the longitudinal direction (X direction). In other words, the opposite end of the robotic arm 2 supports the support unit 12 at the vicinity of the one end of the table 1.

The robotic arm 2 is capable of moving the table 1 with seven degrees of freedom. Specifically, the horizontal articulated assembly 22 provides the robotic arm 2 with three degrees of freedom to rotate about the rotation axis A1 extending in the vertical direction, rotate about a rotation axis A2 extending in the vertical direction, and rotate about a rotation axis A3 extending in the vertical direction. In addition, the vertical articulated assembly 23 provides the robotic arm 2 with three degrees of freedom to rotate about a rotation axis B1 extending in the horizontal direction, to rotate about a rotation axis B2 extending in the horizontal direction, and to rotate about a rotation axis B3 extending in the horizontal direction. In addition, the pitch mechanism 24 provides the robotic arm 2 with one degree of freedom to pitch the table 1 about a rotation axis extending in the transverse direction (Y direction).

The base 21 is buried and fixed in the floor. The base 21 is provided substantially at the center of a movement range of the table 1 in plan view (when viewed in the Z direction).

As illustrated in FIG. 3, the horizontal joints 221 to 223 and the vertical joints 231 to 233 are each provided with a joint driver 4. The horizontal joints 221 to 223 and the vertical joints 231 to 233 are each driven by the joint driver 4 thus provided. The joint driver 4 includes a motor 41, an encoder 42, an electromagnetic brake 43, and a decelerator (not illustrated). The horizontal joints 221 to 223 and the vertical joints 231 to 233 are each rotated about a rotation axis through drive of the motor 41.

The motor 41 includes a servomotor. The motor 41 is driven under control of the controller 3. The electromagnetic brake 43 brakes a joint (the horizontal joints 221 to 223 and the vertical joints 231 to 233). The encoder 42 senses a drive amount of the motor 41 and transmits a result of the sensing to the controller 3. The electromagnetic brake 43 is a non-excitation actuation electromagnetic brake that brakes the motor 41 when the motor 41 is not energized. The electromagnetic brake 43 may be a built-in electromagnetic brake of the motor 41 or an electromagnetic brake externally connected with the motor 41.

As illustrated in FIG. 2, the robotic arm 2 is disposed entirely behind the table 1 in plan view (when viewed in the Z direction). For example, the robotic arm 2 is housed in a housing space below the table 1 when the table 1 is positioned at the surgical operation position. Specifically, the robotic arm 2 is folded completely behind the table 1 in plan view (when viewed in the Z direction) when the table 1 is moved to a position for a surgical operation or treatment on the patient 10 being placed on the table 1. When the robotic arm 2 is folded, the length of the robotic arm 2 in a direction parallel to the longitudinal direction of the table 1 is shorter than half of the length of the table 1 in the longitudinal direction.

The robotic arm 2 causes the table 1 to yaw about an axis extending in the vertical direction (Z direction) by using at least one horizontal joint (at least one of the joints 221, 222, and 223). The robotic arm 2 causes the table 1 to roll about an axis extending in the longitudinal direction (X direction) by using at least one vertical joint (at least one of the joints 231, 232, and 233). The robotic arm 2 causes the table 1 to pitch about an axis extending in the transverse direction (Y direction) by using the pitch mechanism 24.

The controller 3 is a control circuit including, for example, a central processing unit (CPU) 3a, and a memory 3b. The memory 3b according to one or more embodiments may include such devices as a flash memory device, magnetic disk device such as a hard disk drive, and an optical disk device that reads data from a recording medium. In one or more embodiments, the recording medium may include Blu-ray disk, CD-ROM (Compact Disk Read Only Memory), DVD (Digital Versatile Disk). The controller 3 is installed in the base 21 and controls movement of the table 1 by the robotic arm 2. Specifically, the controller 3 controls drive of the robotic arm 2 to move the table 1 based on an operation by a medical person (operator). The controller 3 acquires the posture of the robotic arm 2 and the position and posture of the table 1 based on an output from the encoder 42 of the motor 41 of each joint.

The operation devices 5 and 6 each receive an operation to move the table 1 by the medical person (operator). The operation devices 5 and 6 are each capable of performing an operation of the table 1. The operation device 5 is attached to the table 1 and used. The operation device 6 may be disposed at a position separate from the table 1. The operation devices 5 and 6 are attached to the table 1 through engagement with engagement members provided on side surfaces of the support unit 12 of the table 1. The operation devices 5 and 6 are connected with the controller 3 through wired communication.

Figure 4:
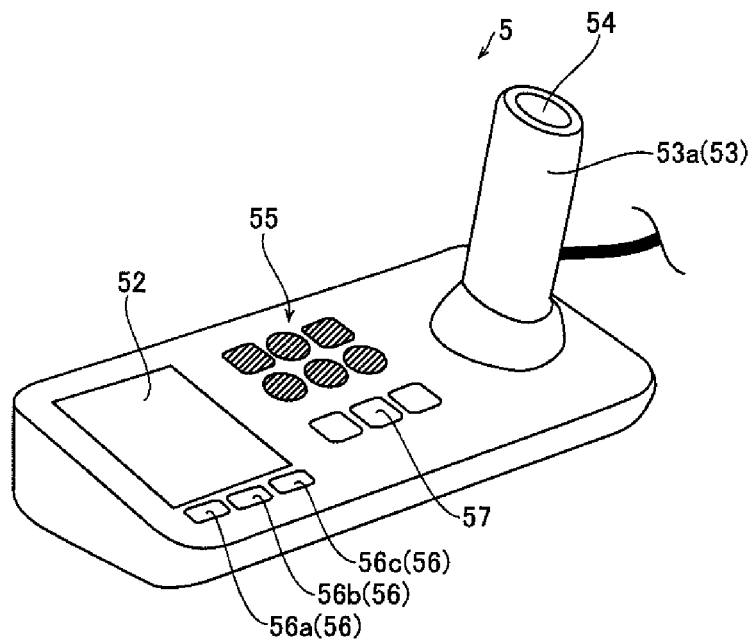
FIG. 4 is a perspective view illustrating an operation device of the robotic operating table according one or more embodiments, which includes a joystick.
Figure 5:
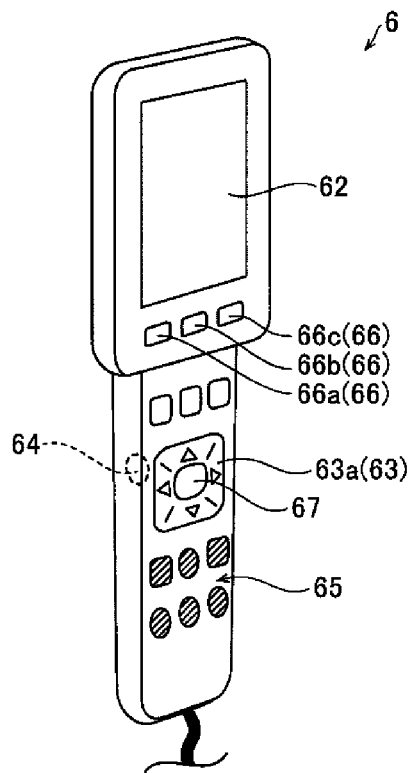
FIG. 5 is a perspective view illustrating an operation device of the robotic operating table according to one or more embodiments, which includes a move direction receiver.

As illustrated in FIGS. 3 and 4, the operation device 5 includes an operation controller 51, a display 52, a move-operation receiving unit 53 including a joystick 53a, a trigger unit 54, an operation mode setting unit 55, a preset position registration setting unit 56, and a moving speed switching button 57. As illustrated in FIGS. 3 and 5, the operation device 6 includes an operation controller 61, a display 62, a move-operation receiving unit 63 including move direction receivers 63a, a trigger unit 64, an operation mode setting unit 65, a preset position registration setting unit 66, and a moving speed switching button 67.

The operation controller 51 (61) controls each component of the operation device 5 (6) based on an operation by the medical person (operator). Specifically, the operation controller 51 (61) controls the display 52 (62) to display an image based on an operation by the medical person (operator). The operation controller 51 (61) transmits operation information to the controller 3 based on an operation by the medical person (operator).

The display 52 (62) displays, for example, the state of the table 1, the state of an operation of the operation device 5 (6), and an operation screen. The display 52 (62) includes a liquid crystal display or an organic electroluminescence (EL) display. In the hybrid operation room 200, the controller 3 of the robotic operating table 100, the operation controller 51 (61) of the operation device 5 (6), and the display 400 (refer to FIG. 1) are connected with each other to perform communication therebetween. The display 400 is capable of displaying, for example, the state of the table 1, the state of an operation of the operation device 5 (6), and the operation screen. The display 400 is capable of displaying, for example, an image displayed by the display 52 (62) of the operation device 5 (6). With this configuration, in the hybrid operation room 200, the operation state of the robotic operating table 100 may be checked by medical persons all at once. The display 400 may be an inputting and display including a touch panel to receive, from a medical person (user) through an operation on a screen, an operation to move the table 1.

The move-operation receiving unit 53 (63) receives, from a user (medical person), a move operation to move the table 1. The move-operation receiving unit 53 of the operation device 5 includes the joystick 53a. The joystick 53a is operated by being tilted. The joystick 53a receives an operation to move the table 1 in accordance with the direction and angle of the tilt. The move-operation receiving unit 63 of the operation device 6 includes the move direction receivers 63a for respective directions in which the table 1 is moved. The move direction receivers 63a are provided for eight directions, for example. Each move direction receiver 63*a* is receives an operation to move the table 1 by being pressed.

The trigger unit 54 (64) is provided to enable the operation of the move-operation receiving unit 53 (63). Specifically, energization of the motor 41 is turned on when the trigger unit 54 (64) is operated. With this configuration, braking of the motor 41 by the electromagnetic brake 43 is released by operating the trigger unit 54 (64). As a result, only while the trigger unit 54 (64) is operated, the operation of the move-operation receiving unit 53 (63) is enabled, so that the table 1 can be moved. In the robotic operating table 100, energization of the motor 41 is turned off when the operation of the trigger unit 54 (64) is released. With this configuration, the motor 41 is braked by the electromagnetic brake 43 by releasing the operation of the trigger unit 54 (64). As a result, when the trigger unit 54 (64) is not operated, the operation of the move-operation receiving unit 53 (63) is disabled, so that the table 1 cannot be moved.

The trigger unit 54 of the operation device 5 is provided at a leading end of the joystick 53*a*. In the operation device 5, the operation of the joystick 53*a* is enabled when the trigger unit 54 is pressed. The operation of the joystick 53*a* is disabled while the pressing on the trigger unit 54 is released. The trigger unit 64 of the operation device 6 is provided on a surface opposite to a surface on which the move direction receivers 63*a* are provided. In the operation device 6, the operation of the move direction receivers 63*a* is enabled when the trigger unit 64 is pressed. The operation of the move direction receivers 63*a* is disabled while the pressing on the trigger unit 64 is released.

The operation mode setting unit 55 (65) is capable of setting a mode in which the table 1 is moved and the posture thereof is changed. Specifically, the operation mode setting unit 55 (65) receives an operation to set an operation mode of the table 1. The operation mode setting unit 55 (65) is provided to set one of operation modes. The operation mode setting unit 55 (65) is capable of setting, as the movement and posture change mode, a pitch mode in which the table 1 is rotated about an axis parallel to the transverse direction (Y direction) of the table 1, a roll mode in which the table 1 is rotated about an axis parallel to the longitudinal direction (X direction) of the table 1, a yaw mode in which the table 1 is rotated about a rotation axis extending in the vertical direction (Z direction) in a horizontal plane, a horizontal movement mode in which the table 1 is linearly moved in a horizontal plane, a vertical movement mode in which the table 1 is vertically moved, and a horizontal posture returning mode. When the trigger unit 54 (64) and the move-operation receiving unit 53 (63) are operated with an operation mode selected by the operation mode setting unit 55 (65), the table 1 is moved.

As illustrated in FIG. 4 (FIG. 5), the operation mode setting unit 55 (65) and the preset position registration setting unit 56 (66) have background colors different from each other. The operation mode setting unit 55 (65) and the move-operation receiving unit 53 (63) have background colors different from each other. In other words, the operation mode setting unit 55 (65) is distinguishable from the preset position registration setting unit 56 (66) and the move-operation receiving unit 53 (63) by color tone. The preset position registration setting unit 56 (66) and the move-operation receiving unit 53 (63) have an identical background color.

The preset position registration setting unit 56 (66) is provided to set a preset position as a movement destination of the table 1 and register the current position of the table 1 as a preset position. When the current position of the table 1 is registered as a preset position by the preset position registration setting unit 56 (66), information on the registered preset position is stored in the memory 3*b* of the controller 3. Specifically, position information of the table 1 and posture information of the robotic arm 2 at that time are stored in the memory 3*b* of the controller 3. A predetermined position is stored as a preset position in the memory 3*b* when a registration operation is received by the preset position registration setting unit 56 (66) while the table 1 is disposed at the predetermined position. When the trigger unit 54 (64) and the move-operation receiving unit 53 (63) are operated with a preset position selected by the preset position registration setting unit 56 (66), the table 1 is moved to the selected preset position.

Figure 6:
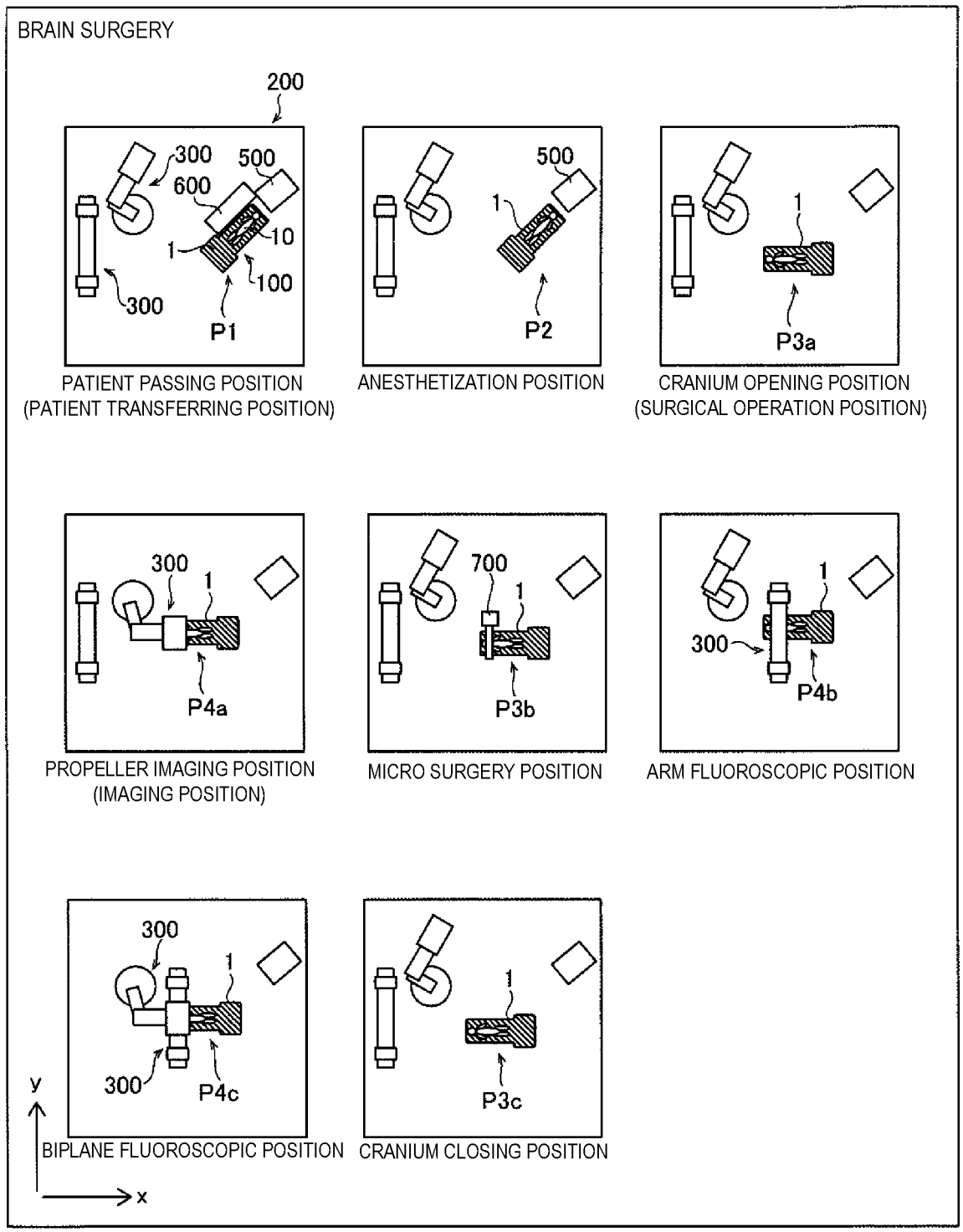
FIG. 6 is a diagram illustrating an example (exemplary brain surgery) of preset positions of a table of the robotic operating table according to one or more embodiments.
Figure 7:
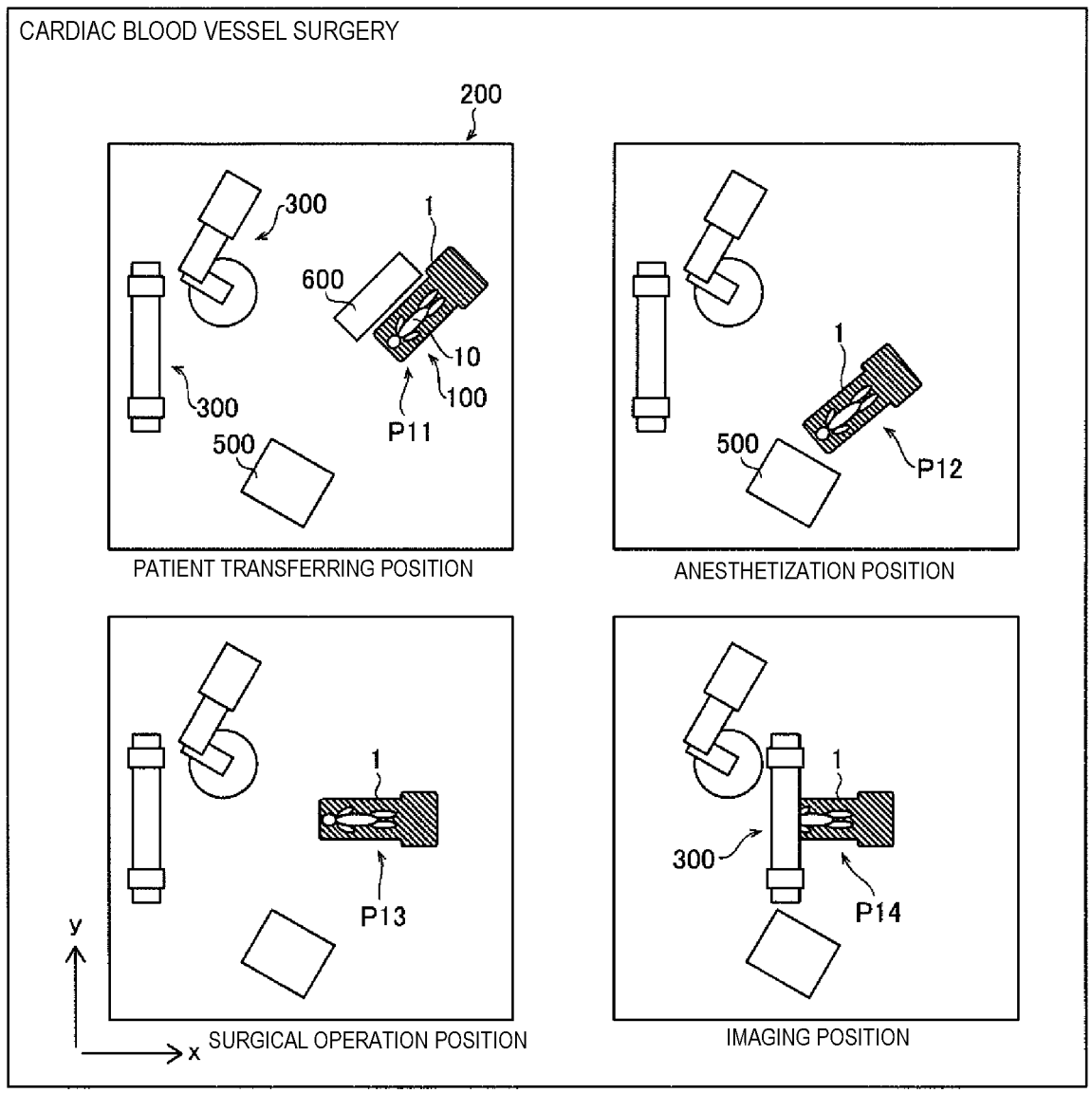
FIG. 7 is a diagram illustrating an example (exemplary cardiac blood vessel surgery) of preset positions of the table of the robotic operating table according to one or more embodiments.
Figure 8:
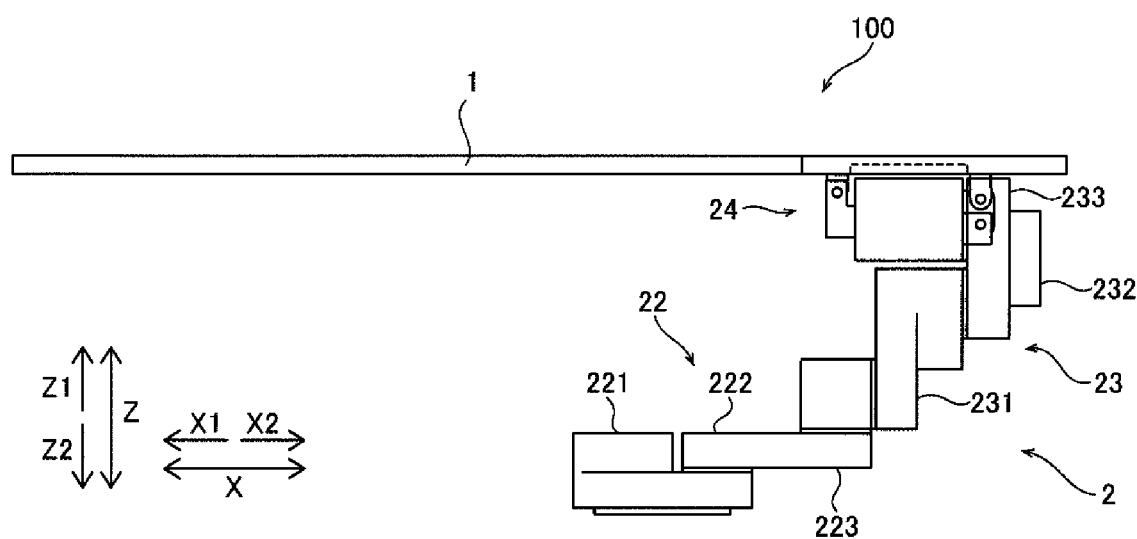
FIG. 8 is a diagram illustrating an exemplary cleaning position of the table of the robotic operating table according to one or more embodiments.

In one or more embodiments, as illustrated in FIGS. 6 and 7, the preset position registration setting unit 56 (66) is capable of registering the anesthetization position, the surgical operation position, and the imaging position as preset positions of the table 1. As illustrated in FIG. 8, the preset position registration setting unit 56 (66) is capable of registering, as a preset position of the table 1, a cleaning position at which to clean the robotic operating table 100. As illustrated in FIGS. 6 and 7, the preset position registration setting unit 56 (66) is capable of registering a patient transferring position as a preset position of the table 1. The preset position registration setting unit 56 (66) is capable of registering the test position and the treatment position as preset positions of the table 1. The preset position registration setting unit 56 (66) is capable of registering an optional position as a preset position of the table 1. The preset position registration setting unit 56 (66) is capable of setting, as a movement destination of the table 1, the patient transferring position, the anesthetization position, the surgical operation position, the test position, the treatment position, the imaging position, the cleaning position, or the optional position thus registered.

For example, as illustrated in FIG. 8, the cleaning position is the position of the table 1 when the robotic arm 2 is extended. Specifically, when the table 1 is positioned at the cleaning position, the horizontal joints 221 to 223 of the horizontal articulated assembly 22 are disposed in an extended manner and the vertical joints 231 to 233 of the vertical articulated assembly 23 are disposed in an extended manner. Accordingly, an overlapping part between the horizontal articulated assembly 22 and the vertical articulated assembly 23 is reduced to allow cleaning to be easily performed.

As illustrated in FIG. 4 (FIG. 5), the preset position registration setting unit 56 (66) includes an anesthetization position registration button 56*a* (66*a*) for registering the anesthetization position, a surgical operation position registration button 56*b* (66*b*) for registering the surgical operation position, and an imaging position registration button 56*c* (66*c*) for registering the imaging position. The anesthetization position registration button 56*a* (66*a*) is used to register the current position of the table 1 as the anesthetization position and set the anesthetization position as a movement destination of the table 1. The surgical operation position registration button 56*b* (66*b*) is used to register the current position of the table 1 as the surgical operation position and set the surgical operation position as a movement destination of the table 1. The imaging position registration button 56*c* (66*c*) is used to register the current position of the table 1 as the imaging position and set the imaging position as a movement destination of the table 1. Any preset position other than the anesthetization position, the surgical operation position, and the imaging position can be registered and set through an operation on a screen displayed on the display 52 (62).

The preset position registration setting unit 56 (66) is capable of registering the anesthetization position, the surgical operation position, and the imaging position as a preset position group for each operative procedure. In addition to the anesthetization position, the surgical operation position, and the imaging position, the preset position registration setting unit 56 (66) may register the patient transferring position as a preset position group for each operative procedure. Examples of the operative procedure include the operative procedures of a cerebral blood vessel operation, a cardiac operation, a blood vessel surgery, a thoracic operation, an abdominal operation, a cranial nerve surgery, an intraneural operation, a cardiac surgery, a cardiovascular internal medicine operation, and an orthopedic surgery.

As illustrated in FIG. 6, in the operative procedure of a brain surgery, the table 1 is positioned at a patient transferring position P1, an anesthetization position P2, a cranium opening position P3a, a propeller imaging position P4a, a micro surgery position P3b, an arm fluoroscopic position P4b, a biplane fluoroscopic position P4c, and a cranium closing position P3c. In the example illustrated in FIG. 6, the anesthetization position P2 as the anesthetization position, the cranium opening position P3a as the surgical operation position, and the propeller imaging position P4a as the imaging position are registered as a preset position group in the operative procedure of a brain surgery. The patient transferring position P1 is the position of the table 1 at which a stretcher 600 on which the patient 10 is transported is positioned alongside the table 1, and is same as the anesthetization position P2. The patient transferring position P1 is also same as the position of the table 1 at which the patient 10 is passed from the table 1 to the stretcher 600 after a surgical operation is completed. The anesthetization position P2 is the position of the table 1 at which the head of the patient 10 is positioned close to an anesthesia device 500. The cranium opening position P3a is the position of the table 1 at which medical persons can stand in a space around the table 1, the radiographic imaging apparatus 300 placed on the floor does not interfere with a surgeon standing near the head of the patient 10, and movement of the patient 10 for image capturing by the radiographic imaging apparatus 300 can be reduced. The propeller imaging position P4a is a position separated from the cranium opening position P3a by 400 mm approximately in the Y direction, and the position of the table 1 at which the head of the patient 10 is positioned close to the radiographic imaging apparatus 300 placed on the floor and a 3D propeller image thereof can be captured by the radiographic imaging apparatus 300 placed on the floor and having a limited image capturing region.

The micro surgery position P3b is the position of the table 1 at which medical persons can stand in a space around the table 1 and the radiographic imaging apparatus 300 placed on the floor does not interfere with a surgeon and an assistant performing a surgical operation while observing an operative field of the head of the patient 10 in an enlarged manner by using a surgical microscope device 700, and is same as the cranium opening position P3a. The arm fluoroscopic position P4b is the position of the table 1 at which fluoroscopy of the right arm of the patient 10 can be performed by the overhead traveling radiographic imaging apparatus 300, and is a position separated from the propeller imaging position P4a and the biplane fluoroscopic position P4c by 400 mm approximately in the Y direction. Thus, to move the table 1 to the arm fluoroscopic position P4b, the table 1 is moved to the imaging position as a preset position and then to the arm fluoroscopic position P4b by operating the move-operation receiving unit 53 (63). The biplane fluoroscopic position P4c is the position of the table 1 at which image capturing can be performed by the radiographic imaging apparatus 300 placed on the floor having a limited image capturing region to perform biplane fluoroscopy of the head of the patient 10 by the radiographic imaging apparatus 300 placed on the floor and the overhead traveling radiographic imaging apparatus 300, and is same as the propeller imaging position P4a. The cranium closing position P3c is same as the cranium opening position P3a.

In the example illustrated in FIG. 7, an anesthetization position P12, a surgical operation position P13, and an imaging position P14 are registered as a preset position group in the operative procedure of a cardiac blood vessel surgery. A patient transferring position P11 is the position of the table 1 at which the stretcher 600 on which the patient 10 is transported can be easily positioned alongside the table 1. The anesthetization position P12 is the position of the table 1 at which the head of the patient 10 is positioned close to the anesthesia device 500. The surgical operation position P13 is the position of the table 1 at which an operator can stand in a space around the table 1 and easily perform a surgical operation. When the surgical microscope device is used, the position of the table 1 is registered with a space for the microscope device taken into account. The imaging position P14 is the position of the table 1 at which the thoracic part of the patient 10 is positioned close to the radiographic imaging apparatus 300 so that image capturing or fluoroscopy thereof is easily performed by the radiographic imaging apparatus 300.

The moving speed switching button 57 (67) is provided to change the moving speed of the table 1. The moving speed of the table 1 is switched at stages at each press on the moving speed switching button 57 (67). For example, the moving speed of the table 1 is switchable between moving speeds at three stages.

In one or more embodiments, the controller 3 controls drive of the robotic arm 2 to move the table 1 to the set preset position when the move-operation receiving unit 63 is operated with a registered preset position set as a movement destination of the table 1. Specifically, while the trigger unit 54 (64) and the move-operation receiving unit 53 (63) are operated together with a registered preset position set as a movement destination of the table 1, the controller 3 controls drive of the robotic arm 2 to move the table 1 toward the preset position. The controller 3 performs control to stop energization of the motor 41 to actuate the electromagnetic brake 43 when the trigger unit 54 (64) is not operated, or control to energize the motor 41 while the trigger unit 54 (64) is operated.

The controller 3 controls drive of the robotic arm 2 to move the table 1 while the trigger unit 54 (64) and the move-operation receiving unit 53 (63) are operated together. Meanwhile, when the table 1 arrives at the preset position, i.e., the position after the movement, the controller 3 performs control that invalidates the operation of the move-operation receiving unit 53 (63) and stops the movement of the table 1. Then, when a user stops the operation of the trigger unit 54 (64), the controller 3 performs control that stops energization of the motor 41 and actuates the electromagnetic brake 43. In this way, the table 1 and the robotic arm 2 are fixed at the preset position immediately. The controller 3 may notify the user of the arrival at the preset position.

In one or more embodiments, while the move-operation receiving unit 53 (63) is operated with a registered preset position set as a movement destination of the table 1, the controller 3 controls the sound output unit 121 to output a sound message indicating that the table 1 will move to the set preset position. For example, when the table 1 is going to move to the registered anesthetization position, the sound output unit 121 outputs a sound message "Moving to the anesthetization position".

While at least one of the move direction receivers 63a is operated with a registered preset position set as a movement destination of the table 1, the controller 3 controls drive of the robotic arm 2 to move the table 1 toward the preset position. Accordingly, if the operation device 6 is enabled to receive an operation by a medical person (operator), the table 1 is moved only while the move direction receiver 63a is operated.

The controller 3 performs control to move the table 1 while the joystick 53a is operated. Specifically, the controller 3 controls drive of the robotic arm 2 to move the table 1 while the joystick 53a is operated. While the joystick 53a is operated with a registered preset position set as a movement destination of the table 1, the controller 3 controls drive of the robotic arm 2 to move the table 1 toward the preset position.

The controller 3 controls drive of the robotic arm 2 to move the table 1 while the trigger unit 54 (64) and the move-operation receiving unit 53 (63) are operated together. Specifically, if the operation device 5 is enabled to receive an operation by a medical person (operator), the table 1 is moved only while the operation of pressing the trigger unit 54 and the operation of tilting the joystick 53a are performed together. If the operation device 6 is enabled to receive an operation by a medical person (operator), the table 1 is moved only while the operation of pressing the trigger unit 64 and the operation of pressing the move direction receivers 63a are performed together.

Figure 9:
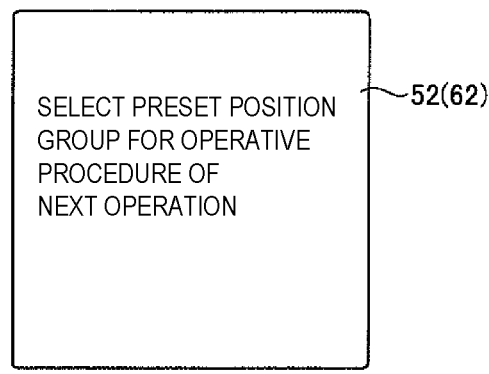
FIG. 9 is a diagram illustrating an exemplary display of the robotic operating table according to one or more embodiments.

In one or more embodiments, as illustrated in FIG. 9, when a power source of the robotic operating table 100 is turned on, the operation controller 51 (61) controls the display 52 (62) and the display 400 to display a message that prompts selection of one of preset position groups registered for respective operative procedures. For example, a message "Select a preset position group for the operative procedure of the next operation" is displayed on the display 52 (62) and the display 400.

Figure 10:
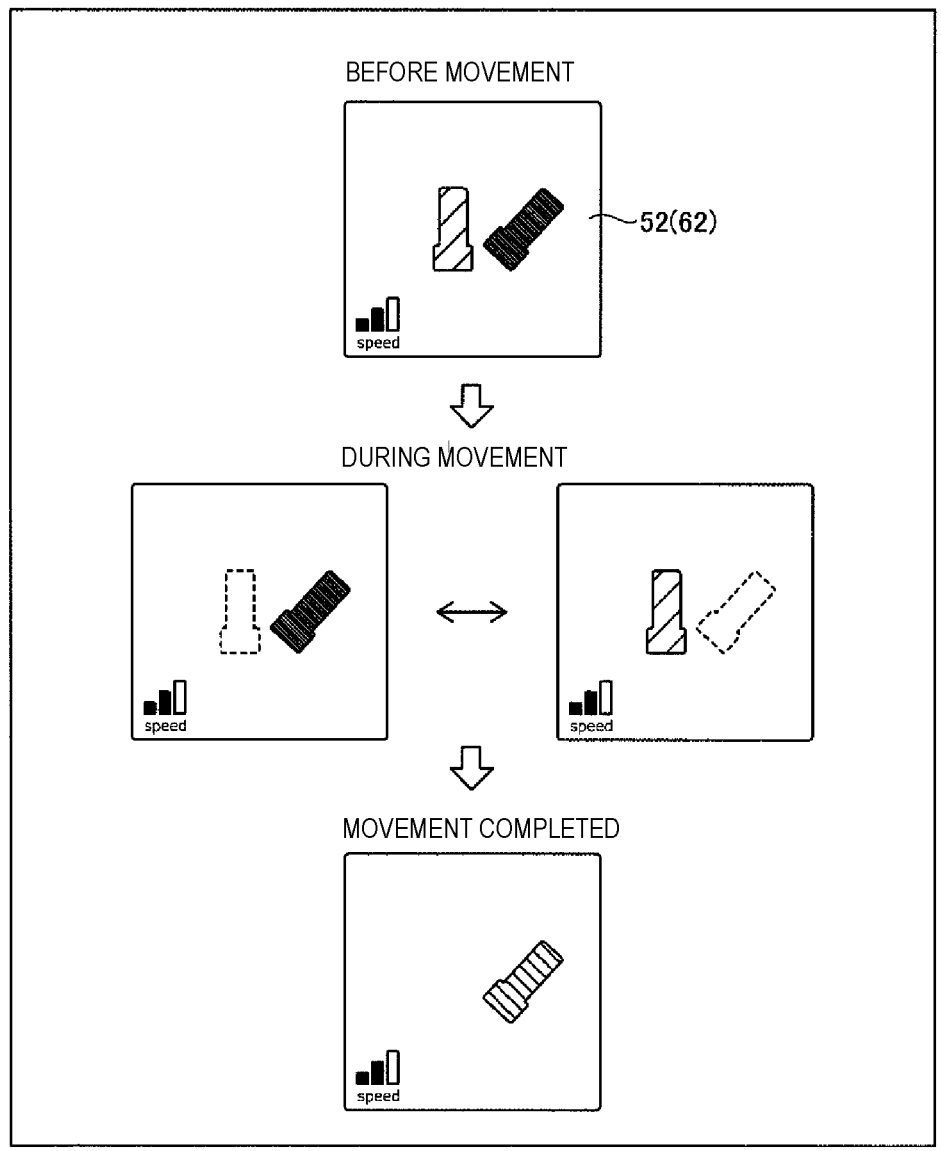
FIG. 10 is a diagram illustrating a display when the table of the robotic operating table is moved according to one or more embodiments.

When a preset position is set as a movement destination of the table 1 by the preset position registration setting unit 56 (66), the operation controller 51 (61) controls the display 52 (62) to display the preset position as a movement destination of the table 1. For example, as illustrated in FIG. 10, the operation controller 51 (61) controls the display 52 (62) to display diagrams (illustrations) representing the table 1 such that the position before the movement and the position after the movement can be distinguished from each other. Before movement of the table 1, the diagrams indicating the position of the table 1 before the movement and the position thereof after the movement are displayed in colors different from each other. During the movement of the table 1, the diagrams indicating the position of the table 1 before the movement and the position thereof after the movement are alternately displayed in a flashing manner. Then, after the movement of the table 1 is completed, only the diagram indicating the position of the table 1 after the movement is displayed.

(Configuration of Radiographic Imaging Apparatus)

The following describes the configuration of the radiographic imaging apparatus 300 with reference to FIG. 1.

As illustrated in FIG. 1, the radiographic imaging apparatus 300 is capable of capturing a radiographic projection image of the patient 10 being placed on the table 1. The X-ray irradiation unit 301 and the X-ray detection unit 302 are supported by the C-arm 303. The X-ray irradiation unit 301 and the X-ray detection unit 302 are moved along with movement of the C-arm 303 and disposed facing to each other on both sides of the patient 10 at the imaging position at radiographic imaging. For example, one of the X-ray irradiation unit 301 and the X-ray detection unit 302 is disposed in a space above the table 1, and the other is disposed in a space below the table 1. At radiographic imaging, the C-arm 303 supporting the X-ray irradiation unit 301 and the X-ray detection unit 302 is disposed in the spaces above and below the table 1.

The X-ray irradiation unit 301 is disposed facing to the X-ray detection unit 302. The X-ray irradiation unit 301 is capable of emitting X-ray toward the X-ray detection unit 302. The X-ray detection unit 302 detects the X-ray emitted by the X-ray irradiation unit 301. The X-ray detection unit 302 includes a flat panel detector (FPD). The X-ray detection unit 302 captures a radiographic image based on detected X-ray. Specifically, the X-ray detection unit 302 converts detected X-ray into an electric signal and transmits the electric signal to an image processing unit (not illustrated).

The C-arm 303 has one end connected with the X-ray irradiation unit 301 and the opposite end connected with the X-ray detection unit 302. The C-arm 303 has a substantially C shape. With this configuration, at radiographic imaging, the C-arm 303 can support the X-ray irradiation unit 301 and the X-ray detection unit 302 while extending around the table 1 and the patient 10 to avoid interference therewith. The C-arm 303 is movable relative to the table 1. Specifically, the C-arm 303 is movable in the horizontal direction and the vertical direction to dispose the X-ray irradiation unit 301 and the X-ray detection unit 302 at desired positions relative to the patient 10 being placed on the table 1, and is also rotatable about a rotation axis extending in the horizontal direction and a rotation axis extending in the vertical direction. The C-arm 303 is moved by a drive unit (not illustrated) based on an operation by a medical person (operator). The C-arm 303 is manually movable by a medical person (operator). The display 400 is capable of displaying a radiographic fluoroscopic image captured by the radiographic imaging apparatus 300, and a radiographic image captured by the radiographic imaging apparatus 300. As illustrated in FIGS. 6 and 7, two radiographic imaging apparatuses 300 may be provided.

Effects of Embodiments

According to one or more embodiments, effects as described below can be obtained.

As described above, one or more embodiments include the preset position registration setting unit 56 (66) and the controller 3. The preset position registration setting unit 56 (66) registers the anesthetization position, the surgical operation position, and the imaging position as preset positions of the table 1 and sets the registered anesthetizing, operating, imaging positions as a movement destination of the table 1. While the move-operation receiving unit 53 (63) is operated with the registered preset position set as a movement destination of the table 1, the controller 3 controls drive of the robotic arm 2 to move the table 1 to the set preset position. With this configuration, the table 1 can be easily moved to preset positions including the anesthetization position, the surgical operation position, and the imaging position. Further, one or more embodiments include the robotic arm 2 including one end supported on the base 21 and the opposite end supporting the table 1. With this configuration, the table 1 can be moved by the robotic arm 2, and thus the movement range and freedom of the table 1 can be increased as compared to a case where the table 1 is moved by a base. Accordingly, the movement range and freedom of the table 1 on which to place the patient 10 can be increased, and the table 1 can be easily moved to a specified position.

In one or more embodiments, the preset position registration setting unit 56 (66) is capable of registering, as a preset position of the table 1, the cleaning position at which to clean the robotic operating table 100. With this configuration, when the robotic operating table 100 is cleaned after a surgical operation, the robotic operating table 100 can be easily moved to a position and a posture at which the robotic operating table 100 can be easily cleaned.

In one or more embodiments, the preset position registration setting unit 56 (66) is capable of registering the patient transferring position as a preset position of the table 1. With this configuration, the table 1 can be easily moved to a patient placement position, when the patient 10 is placed onto the table 1 before a surgical operation and when the patient 10 is moved off the table 1 after the surgical operation, the table 1 can be easily moved to a specified position.

In one or more embodiments, as described above, the preset position registration setting unit 56 (66) is capable of registering an optional position as a preset position of the table 1. With this configuration, the table 1 can be easily moved to an optional position, and thus the patient 10 being placed on the table 1 can be easily moved to an optional position in accordance with a surgical operation method.

In one or more embodiments, as described above, when the move-operation receiving unit 53 (63) is operated with a registered preset position set as a movement destination of the table 1, the controller 3 controls the sound output unit 121 to output a sound message indicating that the table 1 will move to the set preset position. With this configuration, the sound message output from the sound output unit 121 notifies that the table 1 will move to the preset position, and thus a medical person can easily recognize the movement destination of the table 1.

In one or more embodiments, as described above, the controller 3 invalidates the operation of the move-operation receiving unit 53 (63) when the table 1 arrives at the preset position, and then performs control that stops energization of the motor 41 and actuates the electromagnetic brake 43 when the operation of the trigger unit 54 (64) is stopped by a user. With this configuration, the table 1 and the robotic arm 2 are fixed at the preset position after the movement, and thus treatment on the patient 10 can be immediately started. The stopping of energization of the motor 41 at the preset position leads to reduction of power consumption accordingly.

In one or more embodiments, as described above, when a registration operation is received by the preset position registration setting unit 56 (66) while the table 1 is disposed at a predetermined position, the predetermined position is stored as a preset position in the memory 3*b*. With this configuration, the actual position of the table 1 can be registered as a preset position, and thus a position intended by a medical person can be reliably registered as a preset position.

In one or more embodiments, as described above, the preset position registration setting unit 56 (66) is capable of registering, as a preset position group for each operative procedure, the anesthetization position, the surgical operation position, and the imaging position. With this configuration, the table 1 can be moved to the anesthetization position, the surgical operation position, and the imaging position in accordance with an operative procedure. Accordingly, a surgical operation can be smoothly performed in each operative procedure by moving the table 1 to a preset position.

One or more embodiments include the displays 52, 62, and 400 that displays, when the power source of the robotic operating table 100 is turned on, a message that prompts selection of one of preset position groups registered for respective operative procedures. With this configuration, an operative procedure can be selected before the patient 10 is placed on the table 1, and thus the patient 10 being placed on the table 1 can be prevented from being moved without operative procedure selection. Accordingly, the patient 10 can be efficiently moved without unnecessary movement.

In one or more embodiments, as described above, the controller 3 controls drive of the robotic arm 2 to move the table 1 toward the preset position while at least one of the move direction receivers 63*a* is operated with a registered preset position set as a movement destination of the table 1. With this configuration, the table 1 is moved only while the move direction receivers 63*a* is operated, and thus only the operation of the move direction receivers 63*a* just has to be stopped to stop movement of the table 1. Accordingly, the movement of the table 1 can be stopped reliably and immediately.

In one or more embodiments, as described above, while the joystick 53*a* is operated with a registered preset position set as a movement destination of the table 1, the controller 3 controls drive of the robotic arm 2 to move the table 1 toward the preset position. With this configuration, the table 1 is moved only while the joystick 53*a* is operated, and thus only the operation of the joystick 53*a* just has to be stopped to stop movement of the table 1. Accordingly, the movement of the table 1 can be stopped reliably and immediately.

In one or more embodiments, as described above, while the trigger unit 54 (64) and the move-operation receiving unit 53 (63) are operated together, the controller 3 controls drive of the robotic arm 2 to move the table 1. With this configuration, when the move-operation receiving unit 53 (63) is unintentionally operated by a user (medical person), the table 1 is not moved unless the trigger unit 54 (64) is operated. Accordingly, unintentional movement of the table 1 can be effectively prevented.

In one or more embodiments, as described above, the controller 3 performs control that stops energization of the motor 41 and actuates the electromagnetic brake 43 while the trigger unit 54 (64) is not operated, and performs control that energizes the motor 41 while the trigger unit 54 (64) is operated. With this configuration, when the move-operation receiving unit 53 (63) is unintentionally operated by a user (medical person), the table 1 is not moved unless the trigger unit 54 (64) is operated. Accordingly, unintentional movement of the table 1 can be effectively prevented.

In one or more embodiments, as described above, while the trigger unit 54 (64) and the move-operation receiving unit 53 (63) are operated together with a registered preset position set as a movement destination of the table 1, the controller 3 controls drive of the robotic arm 2 to move the table 1 toward the preset position. With this configuration, when the move-operation receiving unit 53 (63) is unintentionally operated with a registered preset position set as a movement destination of the table 1, the table 1 is not moved to the preset position unless the trigger unit 54 (64) is operated. Accordingly, unintentional movement of the table 1 can be effectively prevented.

In one or more embodiments, as described above, the robotic arm 2 includes one end supported on the base 21 to be rotatable about an axis extending in the vertical direction (Z direction), and the opposite end supporting the table 1 at a position near one end of the table 1 in the longitudinal direction (X direction), and moves the table 1 with at least six degrees of freedom. With this configuration, the table 1 can be easily moved to a desired position by the robotic arm 2 having at least six degrees of freedom. The movement range and freedom of the table 1 on which to place the patient 10 can be effectively increased by the robotic arm 2 having at least six degrees of freedom.

In one or more embodiments, as described above, the table 1 includes the table body 11 made of a radiolucent material and the support unit 12 supporting the table body 11, and the opposite end of the robotic arm 2 supports the support unit 12. With this configuration, when the robotic arm 2 is disposed close to the support unit 12 to provide a sufficient space below the table body 11, the radiographic imaging apparatus 300 can be placed below the table body 11 to capture radiographic images of the patient 10 being placed on the table 1.

One or more embodiments include the operation controller 51 (61). When a preset position is set, by the preset position registration setting unit 56 (66), as a movement destination of the table 1, the operation controller 51 (61) controls the display 52 (62) to display the preset position as a movement destination of the table 1. With this configuration, the movement destination of the table 1 can be easily recognized by a medical person.

In one or more embodiments, as described above, the preset position registration setting unit 56 (66) includes the anesthetization position registration button 56a (66a) for registering the anesthetization position, the surgical operation position registration button 56b (66b) for registering the surgical operation position, and the imaging position registration button 56c (66c) for registering the imaging position. With this configuration, the anesthetization position, the surgical operation position, and the imaging position can be easily registered as a preset position in a distinguishable manner.

In one or more embodiments, as described above, the preset position registration setting unit 56 (66) and the move-operation receiving unit 53 (63) have an identical background color, and the operation mode setting unit 55 (65) has a background color different from that of the preset position registration setting unit 56 (66). This configuration may prevent one from mistakenly operating the operation mode setting unit 55 (65) in place of the move-operation receiving unit 53 (63) or the preset position registration setting unit 56 (66) or vice versa, thereby effectively preventing mistakes in operations.

In one or more embodiments, as described above, the operation device 5 (6) includes the moving speed switching button 57 (67) for changing the moving speed of the table 1. With this configuration, the moving speed of the table 1 can be easily changed by the moving speed switching button 57 (67). Since the moving speed of the table 1 is changeable, the moving speed can be decreased to reduce a burden on the patient 10 when the patient 10 is placed on the table 1, and the moving speed can be increased to move the table 1 fast when the patient 10 is not placed on the table 1.

(Modifications)

The embodiments disclosed herein should be considered exemplary in all aspects, non-exhaustive and not limiting. The scope of the present invention is indicated by the claims rather than the explanation of the above embodiments and also embraces all changes that come within the meaning and range of equivalents of the claims.

For example, in one or more embodiments, a hybrid operation room system may include a radiographic imaging apparatus. Additional or alternative embodiments may not be limited to such examples. For example, the hybrid operation room system may include a magnetic resonance imaging apparatus that captures a magnetic resonance image of a patient. Alternatively, the hybrid operation room system may include both of a radiographic imaging apparatus and a magnetic resonance imaging apparatus.

In one or more embodiments, a robotic operating table may be provided in a hybrid operation room. Additional or alternative may not be limited to such examples. For example, the robotic operating table may be provided in an operation room other than the hybrid operation room.

In one or more embodiments, a sound output unit may be provided to a table. Additional or alternative may not be limited to such examples. For example, the sound output unit may be provided to an operation device or may be provided separately from the table and the operation device. Alternatively, the sound output unit may be provided to a robotic arm.

In one or more embodiments, a preset position registration setting unit may be operated by being pressed. Additional or alternative may not be limited to such examples. For example, the preset position registration setting unit may be operated by, for example, sound or gesture. In other words, a preset position may be registered and set through, for example, sound or gesture by a user.

In one or more embodiments, the cranium opening position P3a, the micro surgery position P3b, and the cranium closing position P3c may be the same. Additional or alternative may not be limited to such examples. For example, the cranium opening position P3a, the micro surgery position P3b, and the cranium closing position P3c may be different from each other. When the micro surgery position P3b is slightly separated from the cranium opening position P3a, the cranium opening position P3a may be registered as a preset position of the surgical operation position. Then, when the table 1 is to be moved to the micro surgery position P3b, first, the table 1 may be moved to the cranium opening position P3a by setting, as a movement destination, the surgical operation position (cranium opening position P3a) registered by the preset position registration setting unit, and then may be moved from the cranium opening position P3a to the micro surgery position P3b by operating the move-operation receiving unit 53 (63).

In one or more embodiments, the anesthetization position, the surgical operation position, and the imaging position may be registered as preset positions, but the patient transferring position P1, the anesthetization position P2, the cranium opening position P3a, the propeller imaging position P4a, the micro surgery position P3b, the arm fluoroscopic position P4b, the biplane fluoroscopic position P4c, and the cranium closing position P3c may be all registered as preset positions.

In one or more embodiments, the robotic operating table may be provided with two operation devices. Additional or alternative may not be limited to such examples. For example, the robotic operating table may be provided with one operation device or may be provided with three operation devices or more.

In one or more embodiments, an operation device may be connected with a controller through wired communication. Additional or alternative may not be limited to such examples. For example, the operation device may be connected with the controller through wireless communication.

Figure 11:
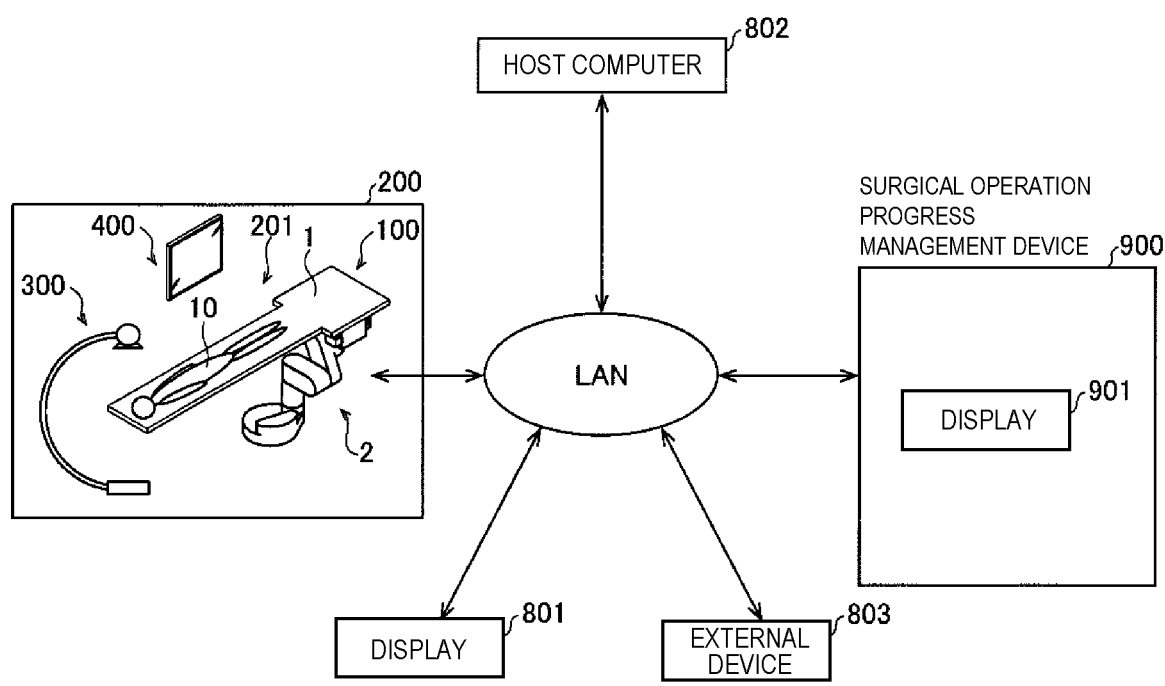
FIG. 11 is a diagram illustrating a display according to a modification of an embodiment.

In one or more embodiments, a display may be provided to an operation device. Additional or alternative may not be limited to such examples. For example, the display may be provided separately from the operation device. In a modification illustrated in FIG. 11, a display provided outside an operation room may display, for example, the state of a table, the state of an operation of an operation device, and an operation screen. Specifically, as illustrated in FIG. 11, the state of the table and the like may be displayed on a display 801 provided outside the hybrid operation room 200 and connected with a local area network (LAN) inside a hospital in which the hybrid operation room 200 is provided. The display 801 is provided at, for example, a nurse station. When a surgical operation progress management device 900 for managing the progress of a surgical operation is provided outside of the hybrid operation room 200, the state of the table and the like may be displayed on a display 901 of the surgical operation progress management device 900. The display 901 of the surgical operation progress management device 900 is provided at, for example, a control center adjacent to the hybrid operation room 200. For example, a host computer 802 and an external device 803 such as a portable terminal owned by hospital staff may be connected with the LAN inside the hospital.

In one or more embodiments, an operation mode setting unit and a move-operation receiving unit may have background colors different from each other. Additional or alternative may not be limited to such examples. For example, the operation mode setting unit and the move-operation receiving unit may provide touch feelings different from each other. For example, the surfaces of the operation mode setting unit and the move-operation receiving unit may have uneven shapes different from each other.

In one or more embodiments, a horizontal articulated assembly may include three horizontal joints. Additional or alternative may not be limited to such examples. For example, the horizontal articulated assembly may include two horizontal joints or may include four horizontal joints or more.

In one or more embodiments, a vertical articulated assembly may include three vertical joints. Additional or alternative may not be limited to such examples. For example, the vertical articulated assembly may include two vertical joints or may include four vertical joints or more.

In one or more embodiments, an articulated robotic arm may include three horizontal joints in a series and three vertical joints in a series. Additional or alternative may not be limited to such examples. For example, the articulated robotic arm may be a vertical articulated robot including parts at which rotation axes of joints adjacent to each other are orthogonal to each other.

In one or more embodiments, the articulated robotic arm may have the seven degrees of freedom. Additional or alternative may not be limited to such examples. For example, the articulated robotic arm may have six or less degrees of freedom or eight or more degrees of freedom, but preferably, may have at least six degrees of freedom.

In one or more embodiments, a base may be buried and fixed in the floor. Additional or alternative may not be limited to such examples. For example, the base may be fixed on the floor.

In one or more embodiments, the controller 3 may be disposed in the base 21. Additional or alternative may not be limited to such examples. For example, the controller 3 may be housed in a control box, and the control box may be disposed at an optional position inside the hybrid operation room 200 or the control center adjacent to the hybrid operation room 200.

In one or more embodiments, the controller 3 may perform control to stop movement of the table 1 by invalidating the operation of the move-operation receiving unit 53 (63) when the table 1 arrives at a preset position, and to stop energization of the motor 41 and actuate the electromagnetic brake 43 when the operation of the trigger unit 54 (64) is stopped by a user. Additional or alternative may not be limited to such examples. For example, when the table 1 arrives at a preset position, the controller 3 may stop energization of the motor 41 and actuate the electromagnetic brake 43 even though the move-operation receiving unit 53 (63) and the trigger unit 54 (64) are operated together.

In the case of such a conventional operating table as disclosed in Japanese Patent Application Publication No. 2014-100301, the table may have a small movement range in the horizontal directions and poor freedom of movement. Thus, it may be difficult to move the table to various positions (such as an anesthetization position, a surgical operation position, and an imaging position) by increasing the movement range and freedom of the table. In addition, in the case of such an operating table, the small movement range of the operating table may make it difficult to leave sufficient spaces around the positions at which medical persons such as surgeons, assistants, nurses, and medical technicians stand, and therefore may make it difficult for them to perform a surgical operation. It may be also impossible to move the table to a desired position specified among various positions (such as the anesthetization position, the surgical operation position, and the imaging position).

One or more embodiments described above provide a robotic operating table, a hybrid operation room, and a robotic operating table operation device which achieve increases in the movement range and freedom of a patient placement table, and enable the table to be easily moved to a specified position.

The above-described aspects may be combined with each other as practicable within the contemplated scope of embodiments. The above described embodiments are to be considered in all respects as illustrative, and not restrictive. The illustrated and described embodiments may be extended to encompass other embodiments in addition to those specifically described above without departing from the intended scope of the invention. The scope of the invention is to be determined by the appended claims when read in light of the specification including equivalents, rather than solely by the foregoing description. Thus, all configurations including configurations that fall within equivalent arrangements of the claims are intended to be embraced in the invention.

What is claimed is:
1. A robotic operating table comprising:
a patient placement table;
a robotic arm comprising a plurality of joints, and having a first end supported on a base and a second end supporting the patient placement table; and an operation device comprising a preset position registration setting unit that registers an anesthetization position, a surgical operation position, and an imaging position and sets one of the registered anesthetization, surgical operation, and imaging positions as a movement destination of the patient placement table, and a move-operation receiving unit that receives, from a user, a move operation to move the patient placement table, wherein:
when the move-operation receiving unit is operated while one of the registered anesthetization, surgical operation, and imaging positions is set as the movement destination of the patient placement table, the robotic arm moves the patient placement table to the set one of the registered anesthetization, surgical operation, and imaging positions.

2. The operating table according to claim 1, wherein the preset position registration setting unit is configured to register a cleaning position at which to clean the robotic operating table, and set the registered cleaning position as the movement destination of the patient placement table.

3. The operating table according to claim 1, wherein the preset position registration setting unit is configured to register a patient transferring position and set the registered patient transferring position as the movement destination of the patient placement table.

4. The operating table according to claim 1, wherein the preset position registration setting unit includes at least an anesthetization position registration setting unit, a surgical operation position registration setting unit, and an imaging position registration setting unit.

5. The operating table according to claim 1, further comprising a sound output unit, wherein, when the move-operation receiving unit is operated while the one of the registered anesthetization, surgical operation, and imaging positions is set as the movement destination of the patient placement table, the sound output unit outputs a sound message indicating that the patient placement table is going to move to the set one of the registered anesthetization, surgical operation, and imaging positions.

6. The operating table according to claim 1, wherein
each of the joints includes a motor and an electromagnetic brake, and
after the patient placement table is disposed at the set one of the registered anesthetization, surgical operation, and imaging positions, the robotic arm fixes a posture by stopping energization of the motor and actuating the electromagnetic brake.

7. The operating table according to claim 1, wherein, when the preset position registration setting unit receives an operation to register one of the anesthetization, the surgical operation, and the imaging positions while the patient placement table is disposed at a predetermined position, the predetermined position is registered as one of the registered anesthetization, the surgical operation, and the imaging positions.

8. The operating table according to claim 1, wherein the preset position registration setting unit is capable of registering the anesthetization position, the surgical operation position, and the imaging position as a preset position group for each operative procedure.

9. The operating table according to claim 8, further comprising a display that displays, when a power source of the robotic operating table is turned on, a message prompting selection of one preset position group from among the preset position groups registered for respective operative procedures.

10. The operating table according to claim 1, wherein
the move-operation receiving unit includes move direction receivers provided individually for directions in which to move the patient placement table, and
the robotic arm moves the patient placement table toward the set one of the registered anesthetization, surgical operation, and imaging positions when at least one of the move direction receivers is operated while the one of the registered anesthetization, surgical operation, and imaging positions is set as the movement destination of the patient placement table.

11. The operating table according to claim 1, wherein
the move-operation receiving unit includes a joystick, and
the robotic arm moves the patient placement table toward the set one of the registered anesthetization, surgical operation, and imaging positions when the joystick is operated while the one of the registered anesthetization, surgical operation, and imaging positions is set as the movement destination of the patient placement table.

12. The operating table according to claim 1, wherein
the operation device includes a trigger unit that enables operation of the move-operation receiving unit, and
the robotic arm moves the patient placement table while the trigger unit and the move-operation receiving unit are operated together.

13. The operating table according to claim 12, wherein the robotic arm moves the patient placement table toward the set one of the registered anesthetization, surgical operation, and imaging positions when the trigger unit and the move-operation receiving unit are operated together while the one of the registered anesthetization, surgical operation, and imaging positions is set as the movement destination of the patient placement table.

14. The operating table according to claim 1, wherein
the operation device includes a trigger unit,
each of the joints includes a motor and an electromagnetic brake, and
the robotic arm stops energization of the motor and actuate the electromagnetic brake while the trigger unit is not operated, or energizes the motor and does not actuate the electromagnetic brake while the trigger unit is operated.

15. The operating table according to claim 1, wherein
the first end of the robotic arm is supported on the base to be rotatable about an axis extending in a vertical direction,
the second end of the robotic arm supports the patient placement table at a position near the first end in a longitudinal direction of the patient placement table, and
the robotic arm moves the patient placement table with at least six degrees of freedom.

16. The operating table according to claim 1, wherein
the patient placement table includes a table body made of a radiolucent material and a support unit supporting the table body, and
the second end of the robotic arm supports the support unit.

17. The operating table according to claim 1, wherein
the operation device comprises a trigger unit that enables operation of the move-operation receiving unit,
the patient placement table is moved only when the move-operation receiving unit and the trigger unit are operated together by the user while the one of the registered anesthetization, surgical operation, and imaging positions is set as the movement destination of the patient placement table.

18. The operating table according to claim 1, wherein
the move-operation receiving unit comprises move direction receivers provided respectively for directions in which to move the table, and
when any one of the move direction receivers is operated in the condition in which the one of the registered anesthetization, surgical operation, and imaging positions is set as the movement destination of the patient placement table, the robotic arm moves the patient placement table to the set one of the registered anesthetization, surgical operation, and imaging positions.

19. The operating table according to claim 1, wherein
the move-operation receiving unit comprises a joystick to move the table, and
when the joystick is operated in any direction in the condition in which the one of the registered anesthetization, surgical operation, and imaging positions is set as the movement destination of the patient placement table, the robotic arm moves the patient placement table to the set one of the registered anesthetization, surgical operation, and imaging positions.

20. A robotic operating table comprising:
a patient placement table;
a robotic arm comprising a plurality of joints, and having a first end supported on a base and a second end supporting the patient placement table;
an operation device including a preset position registration setting unit that registers an anesthetization position, a surgical operation position, and an imaging position and sets one of the registered anesthetization, surgical operation, and imaging positions as a movement destination of the patient placement table, and a move-operation receiving unit that receives, from a user, a move operation to move the patient placement table; and
a sound output unit, wherein:
when the move-operation receiving unit is operated while one of the registered anesthetization, surgical operation, and imaging positions is set as the movement destination of the patient placement table, the sound output unit outputs a sound indicating that the patient placement table is moving.

21. A hybrid operation system comprising:
a robotic operating table; and
at least one of a radiographic imaging apparatus that captures a radiographic projection image of a patient and a magnetic resonance imaging apparatus that captures a magnetic resonance image of the patient,
wherein the robotic operating table comprises:
a patient placement table;
a robotic arm comprising a plurality of joints, and having a first end supported on a base and a second end supporting the patient placement table; and
an operation device including a preset position registration setting unit that registers an anesthetization position, a surgical operation position, and an imaging position and sets one of the registered anesthetization, surgical operation, and imaging positions as a movement destination of the patient placement table, and a move-operation receiving unit that receives, from a user, a move operation to move the patient placement table; wherein:
when the move-operation receiving unit is operated while one of the registered anesthetization, surgical operation, and imaging positions is set as the movement destination of the patient placement table, the robotic arm moves the patient placement table to the set one of the registered anesthetization, surgical operation, and imaging positions.

22. A robotic operating table operation device comprising:
a preset position registration setting unit that registers an anesthetization position, a surgical operation position, and an imaging position and sets one of the registered anesthetization, surgical operation, and imaging positions as a movement destination of a patient placement table of a robotic operating table;
a move-operation receiving unit that receives, from a user, a move operation to move the patient placement table; and
a display, wherein:
the robotic operating table includes the patient placement table, and a robotic arm comprising a plurality of joints, and having a first end supported on a base and a second end supporting the patient placement table;
when one of the registered anesthetization, surgical operation, and imaging positions is set as a movement destination of the patient placement table, the display displays the set position of the movement destination of the patient placement table.

23. The operation device according to claim 22, wherein the preset position registration setting unit is capable of registering the anesthetization position, the surgical operation position, and the imaging position as a preset position group for each operative procedure.

24. The operation device according to claim 23, wherein, when a power source of the robotic operating table is turned on, the display displays a message prompting selection of one preset position group from among the preset position groups registered for respective operative procedures.

25. The operation device according to claim 22, wherein the preset position registration setting unit includes at least an anesthetization position registration setting unit, a surgical operation position registration setting unit, and an imaging position registration setting unit.

26. The operation device according to claim 22, further comprising an operation mode setting unit that sets an operation mode of the robotic operating table, wherein
the preset position registration setting unit and the move-operation receiving unit have an identical background color, and
the operation mode setting unit has a background color different from the background color of the preset position registration setting unit.

27. The operation device according to claim 22, further comprising a moving speed switching button that changes a moving speed of the patient placement table.

* * * * *